(12) United States Patent
O'Sullivan et al.

(10) Patent No.: US 9,103,831 B2
(45) Date of Patent: Aug. 11, 2015

(54) ORALLY ADMINISTERED BACTERIA AS VEHICLES FOR SYSTEMIC DELIVERY OF AGENTS

(75) Inventors: Gerald O'Sullivan, Curaheen (IE); Brendan O'Sullivan, legal representative, Curaheen (IE); Mark Tangney, Glanmire (IE); Douwe Van Sinderen, Carrigrohane (IE); Michelle Cronin, Belgooly (IE)

(73) Assignee: University College Cork-National University of Ireland Cork, Cork (IE)

( * ) Notice: Subject to any disclaimer, the term of this patent is extended or adjusted under 35 U.S.C. 154(b) by 78 days.

(21) Appl. No.: 13/384,157

(22) PCT Filed: Jul. 16, 2010

(86) PCT No.: PCT/EP2010/060363
§ 371 (c)(1),
(2), (4) Date: Mar. 22, 2012

(87) PCT Pub. No.: WO2011/007007
PCT Pub. Date: Jan. 20, 2011

(65) Prior Publication Data
US 2012/0189550 A1    Jul. 26, 2012

(30) Foreign Application Priority Data
Jul. 16, 2009    (EP) .................................... 09165716

(51) Int. Cl.
*A61K 35/745*    (2015.01)
*A61K 47/48*     (2006.01)
*G01N 33/574*    (2006.01)
*A61K 6/00*      (2006.01)
*A61K 35/00*     (2006.01)
*A61K 48/00*     (2006.01)
*A61K 35/74*     (2015.01)
*A61K 49/00*     (2006.01)

(52) U.S. Cl.
CPC .............. *G01N 33/574* (2013.01); *A61K 35/74* (2013.01); *A61K 47/48776* (2013.01); *A61K 48/0075* (2013.01); *A61K 49/0097* (2013.01); *A61K 2035/115* (2013.01)

(58) Field of Classification Search
None
See application file for complete search history.

(56) References Cited

FOREIGN PATENT DOCUMENTS

| EP | 1281772 A1 | 2/2003 |
| WO | 02068662 A1 | 9/2002 |
| WO | 03006069 A1 | 1/2003 |
| WO | 2008115061 A2 | 9/2008 |
| WO | 2010055499 A2 | 5/2010 |

OTHER PUBLICATIONS

Cronin et al. BMC Microbiology 8: 161: 1-12, Sep. 24, 2008.*
Fu et al. Cancer Gene Therapy 12: 133-140, 2005.*
Cronin et al. Molecular Therapy 18: 1397-1407, Jul. 2010.*
International Search Report dated Dec. 13, 2010 for International Application No. PCT/EP2010/060363.

* cited by examiner

*Primary Examiner* — S. Devi
(74) *Attorney, Agent, or Firm* — Christopher & Weisberg, P.A.

(57) ABSTRACT

The current invention relates to the use of a bacterial species in the preparation of a composition adapted for oral administration for the delivery of an agent to a site in the body. The site in the body may be an organ or a tumour site. The bacterial species is a food grade, non-pathogenic, gram-positive bacteria capable of anaerobic growth.

3 Claims, 9 Drawing Sheets

ORALLY ADMINISTERED BACTERIA AS VEHICLES FOR SYSTEMIC DELIVERY OF AGENTS

CROSS-REFERENCE TO RELATED APPLICATIONS

This application is a 35 U.S.C §371 of International Application No. PCT/EP2010/060363, filed Jul. 16, 2010, which application claims priority to European Patent Application Ser. No. 09165716.3 filed Jul. 16, 2009, the entirety of all of which are incorporated herein by reference.

FIELD OF THE INVENTION

The current invention relates to bacterial translocation. More specifically the current invention relates to bacteria, in particular orally administered bacteria, as a vehicle for delivery of agents to a site in the body.

BACKGROUND TO THE INVENTION

The current challenges facing oncology practitioners and researchers include the development of specific treatments and efficient tumour detection methods. Genetically modified, pathogenic and non-pathogenic bacteria have begun to emerge as potential biological agents with natural tumour specificity. Several bacterial species or genera (e.g. *Escherichia coli, Bifidobacterium*, attenuated *Salmonella typhimurium, Clostridium, Vibrio cholera, Listeria monocytogenes*) have been demonstrated to localise to and replicate in tumour tissue when intravenously administered in rodent models. Achieved through anaerobic bacterial targeting, specific localisation of species, such as members of the *Bifidobacterium* genus, in hypoxic regions of tumours after intravenous administration has been reported.

The term bacterial translocation refers to trafficking of viable bacteria from the Gastro-Intestinal Tract (GIT) to extraintestinal sites. This phenomenon is well studied in bacterial sepsis linked with various conditions [14,15]. The three primary mechanisms promoting bacterial translocation in animal models are identified as: (a) disruption of the ecologic GI equilibrium to allow intestinal bacterial overgrowth, (b) increased permeability of the intestinal mucosal barrier, and (c) deficiencies in host immune defences. These mechanisms can act in concert to synergistically promote the systemic spread of indigenous translocating bacteria to cause lethal sepsis. In animal models in which the intestinal barrier is not physically damaged, pathogenic bacteria may translocate by an intracellular route through the epithelial cells lining the intestines and then travel via the lymph to the mesenteric lymph node (MLN). In animal models exhibiting damage to the mucosal epithelium, indigenous bacteria translocate intercellularly between the epithelial cells to directly access the blood. Indigenous gastro-intestinal (GI) bacteria have been cultured directly from the MLN of various types of patients. Thus, evidence is accumulating that translocation of indigenous bacteria from the GI tract is an important early step in the pathogenesis of opportunistic infections originating from the GI tract. Sampling from humans has indicated that translocation may be a phenomenon that occurs in healthy individuals and may be a normal physiologic event without deleterious consequences [48].

Bifidobacteria are a native, harmless resident of the human gut, and certain bifidobacterial strains have been shown to have health-promoting or probiotic benefits. A number of bifidobacterial strains that harbour plasmids expressing therapeutic agents, such as endostatin or prodrug activating enzymes, have been shown to induce regression in rodent tumour models when administered intravenously [33]. Live imaging of mice has shown intravenously administered lux tagged invasive pathogenic bacteria replicating locally in tumours. No imaging of bifidobacteria in tumours has been reported.

To date, bacterial localisation to tumours has been described only with intravenous administration. Fu et al previously described use of *B. longum* to deliver a therapeutic peptide to the GIT [33]. *B. longum* expressing endostatin was administered orally to athymic mice, and the authors reported that subsequent gut absorption of the therapeutic peptide resulted in slowing in the growth of subcutaneous (s.c.) liver tumours. Translocation of bacteria from the gut to tumours was not reported. Several studies have investigated the ability of bifidobacterial colonisation of the GIT to inhibit translocation of pathogens [16]. A study from 1985 demonstrated *B. longum* colonisation of organs post feeding [47]. The authors reported very low bacterial counts in the kidney and liver however. In addition the authors did not report bacterial translocation to tumour cells.

Despite the teachings of the prior art, the current inventors have surprisingly demonstrated translocation of a non-pathogenic species of bacteria following oral administration, utilising a lux luminescence-based tagging system in *Bifidobacteria breve* in mice, with subsequent growth specifically in tumours. *B. breve* UCC2003 carrying the plasmid pLuxMC3 [18] was orally administered to athymic MF1 nu/nu mice bearing subcutaneous (s.c.) B16-F10 murine melanoma tumours (FIG. 1*a*). By transfection with plasmids that are suitable for bacterial replication expression of heterologous genes, such bacteria can home to tumours, replicate within them and locally express therapeutic proteins. It would not have previously been expected by those skilled in the art that non-pathogenic viable species of bacteria would translocate to tumours in hosts.

The current invention has the added advantage in that it necessitates oral administration, which is relatively painless and offers greater flexibility for use in a range of clinical situations and is of particular benefit for paediatric patients. The administration of therapeutic agents intravenously, as described previously, is painful and causes patient discomfort.

OBJECT OF THE INVENTION

It is an object of the current invention to provide a bacterial species for use as a vehicle to deliver agents. The agents and/or the bacterial species are delivered to a site in the body, which may be an organ or a tumour or the bloodstream. A further object of the current invention is to provide a method of tumour detection, a method of tumour imaging, a method of monitoring the effectiveness of tumour treatment, a method of tumour staging, a method of detecting tumour metastasis, and/or in a method of tumour or cancer treatment. It is a further object of the invention to provide a therapeutic agent for the treatment of disease.

SUMMARY OF THE INVENTION

A Sequence Listing as a text file has been filed in the present application, in computer readable form, via EFS-Web. The Sequence Listing is provided as a file entitled 1711-2PUS_Sequence_Listing_ST25.txt created on Jul. 1, 2013 (Patent In version 3.5), which is 792 bytes in size. The information in computer readable form is incorporated herein by reference in its entirety.

According to the first aspect of the current invention there is provided a bacterial species adapted for oral administration in the preparation of a composition for the delivery of an agent to a site in the body. In a preferred embodiment, the bacterial species is deliverable to a site in the body and is capable of expressing or producing an agent at the site.

In one embodiment the agent and/or bacterial species is deliverable to an organ. The organ may be any organ of the body. The site in the body may be an organ, or the bloodstream or a tumour site. In a preferred embodiment the bacterial species is viable.

In a still further embodiment there is provided a bacterial species adapted for oral administration in the preparation of a composition for the delivery of an agent to a tumour, wherein the bacterial species is deliverable to the tumour. In a still further embodiment there is provided a bacterial species adapted for oral administration in the preparation of a composition for the delivery of an agent to the bloodstream, wherein the bacterial species is deliverable to the bloodstream.

In a preferred embodiment the agent and/or bacterial species is deliverable to a tumour site. In this preferred embodiment the composition or bacterial species may be adapted for or is for use in a method of tumour detection, a method of tumour imaging, a method of monitoring the effectiveness of tumour treatment, a method of tumour staging, a method of detecting tumour metastasis, and/or in a method of tumour or cancer treatment. The method of tumour detection and treatment may occur simultaneously. The agent may be an imaging agent, such as a fluorescent protein (e.g. RFP, GFP) a substrate-converting enzyme (e.g., Luciferase, bacterial lux operon, Alkaline Phosphatase, B-Galactosidase), or image contrast-enhancing agent. Alternatively the agent may be a tumour suppressing agent, such as an anti-angiogenic agent (e.g. endostatin, angiostatin, IL12, IL23, IL32), an immune cell regulating agent (cytokine or other), a secreted peptide, a tumour associated antigen, an antibody, a pro-apoptotic peptide (e.g. IL23), or a cell signalling interfering peptide (e.g. IL32).

In one embodiment the agent is encoded on a vector capable of expressing at least one exogenous gene. The bacterial species of the invention is transformed with the vector. The invention provides a bacterial species transformed with a vector capable of expressing at least one exogenous gene, adapted for oral administration in the preparation of a composition for the delivery of an agent to a site in the body. In a further embodiment the agent is linked to the bacterial species of the invention. The agent may be linked, bonded, fixed or chemically coupled or attached to the bacterial species or the bacterial membrane or attached/linked by any other means known to the skilled person.

The gene may encode an agent selected from the group comprising an imaging agent, such as a fluorescent protein (e.g. RFP, GFP) a substrate converting enzyme (e.g., Luciferase, bacterial lux operon, Alkaline Phosphatase, B-Galactosidase), an image contrast enhancing agent, a tumour suppressing agent, such as an anti-angiogenic agent (e.g. endostatin, angiostatin, IL12, IL23, IL32), an immune cell regulating agent (cytokine or other), a secreted peptide, a tumour associated antigen, an antibody, a pro-apoptotic peptide (e.g. IL23), or a cell signalling interfering peptide (e.g. IL 32).

In all embodiments, the bacterial species may be any food grade, non-pathogenic, gram-positive bacteria capable of anaerobic growth. The bacterial species may be viable. The bacteria may be a Bifidobacteria selected from the group comprising B. breve, B. adolescentis, B. angulatum, B. bifidum, B. parvolulorum, B. catenulatum, B. denticolens, B. dentium, B. gallicum, B. infantis, B. liberorum, B. lactenti, B. inopinaturn, B. longum, B. pseudocatenulatum, B. lactis, B. animatis, B. minimum, B. subtile, B. thermacidophilum, B. asteroids, B. boum, B. choerinum, B. coryneforme, B. cuniculi, B. gallinarum, B. indicum, B. magnum, B. merycicum, B. pseudolongum, B. pullorum, B. ruminantium, B. saeculare, B. suis, B. thermophilum, B. ruminate, B. asteroids, B. boum, B. gallinarum, B. minimum.

The bacteria may be a *Lactobacillus* species selected from the group comprising L. acetototerans, L. acidifarinae, L. acidipiscis, L. acidophilus, L. agilis, L. algidus, L. atimentarius, L. amytolyticus, L. amylophilus, L. amylotrophicus, L. amylovorus, L. animatis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii subsp. delbrueckii, L. delbrueckii subsp. butgaricus, L. delbrueckii subsp. lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hitgardii, L. homohiochii, L. iners, L. ingluviei, L. intestinalis, L. jensenii, L. johnsonii, L. katixensis, L. kefiranofaciens, L. kefiri, L. kimchii, L. kitasatonis, L. kunkeei, L. leichmannii, L. lindneri, L. malefermentans, L. mati, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracollinoides, L. parafarraginis, L. parakefiri, L. paratimentarius, L. paraplantarum, L. pentosus, L. perolens, L. plantarum, L. pontis, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae, L. zymae.

The bacteria may be a *Lactococcus* species selected from the group comprising L. garvieae, L. lactis, L. piscium, L. plantarum, L. raffinolactis.

In another aspect, the current invention provides a method of delivering an agent to a tumour site comprising the use of a bacterial species adapted for oral delivery. The invention also provides a method of deliverying an agent to the bloodstream comprising the use of a bacterial species adapted for oral delivery, which may enable body-wide circulation of bacteria. In such methods the bacterial species is deliverable to the tumour or the bloodstream. The bacterial species may be any food grade, non-pathogenic, gram-positive bacteria capable of anaerobic growth.

In another embodiment the current invention provides a method of delivering an agent to a site in the body, such as an organ or a tumour site or the bloodstream, comprising the use of a bacterial species adapted for oral delivery. The bacterial species may be deliverable to the site in the body. The method comprising orally administering a composition to a subject, the composition comprising a bacterial species containing a vector capable of expressing at least one exogenous gene, wherein the bacterial species targets a site in the body and the gene is expressed within or adjacent to the site in the body. The bacterial species may be any food grade, non-pathogenic, gram-positive bacteria capable of anaerobic growth.

The invention further provides a method of tumour detection or tumour imaging comprising orally administering a composition comprising, a bacterial species containing a vector capable of expressing at least one exogenous gene, wherein the bacterial species targets the tumour environment and the gene is expressed within or adjacent to the targeted tumour. The method further comprises external imaging and/or detecting/measuring the expression of the gene, to determine the targeted sites in the body to allow detection/imaging of said tumours in the body.

The invention further provides a method of monitoring the effectiveness of tumour treatment, tumour staging or detecting tumour metastasis comprising orally administering a composition comprising, a bacterial species containing a vector capable of expressing at least one exogenous gene, wherein the bacterial species targets the tumour environment and the gene is expressed within the targeted tumour. The method further comprises external imaging and/or detecting/measuring the expression of the gene, to determine the targeted sites in the body to allow the monitoring the effectiveness of tumour treatment, tumour staging or detecting tumour metastasis of said tumours in the body.

The gene may encode an agent selected from the group comprising an imaging agent, such as a fluorescent protein (e.g. RFP, GFP) a substrate converting enzyme (e.g., Luciferase, bacterial lux operon, Alkaline Phosphatase, B-Galactosidase), an image contrast enhancing agent, a tumour suppressing agent, such as an anti-angiogenic agent (e.g. endostatin, angiostatin, IL12, IL23, IL32), an immune cell regulating agent (cytokine or other), a secreted peptide, a tumour associated antigen, an antibody, a pro-apoptotic peptide (e.g. IL23), or a cell signalling interfering peptide (e.g. IL 32).

It is a further aspect of the invention to provide a bacterial species adapted for oral administration in the preparation of a composition for the delivery of an agent to a site in the body wherein the composition is adapted for use as a therapeutic agent for the treatment of disease and/or a diagnostic agent for the detection of disease. The site may be an organ, a tumour or the bloodstream.

The term "vector" used herein refers to any DNA material capable of transferring genetic material into a host organism. The vector may be linear or circular in topology and includes but is not limited to plasmids, food grade plasmids, DNA bacteriophages or DNA viruses.

BRIEF DESCRIPTION OF THE DRAWINGS

The current invention will now be described with reference to the following examples and figures. It is to be understood that the following detailed description and accompanying figures, are exemplary and explanatory only and are intended to provide a further explanation of the present invention, as claimed and not to limit the scope of the invention in any way.

(b, c) Trafficking of UCC2003 to subcutaneous tumours B. breve UCC2003 following either oral (b) or intravenous (c) oral delivery, displaying recovery from s.c. tumour tissue and other organs (bars, y axis) and lux expression in vivo in live MF1 nu/nu mice (squares, z axis and images). Increase in bacterial numbers and plasmid gene expression specifically in tumours was observed over time. Low levels of B. breve colony forming units were detected in all organs examined from all treated animals (≤100 cfu/organ; no detectable luminescence).

(d) Comparative recovery of UCC2003 from subcutaneous tumours following either oral or intravenous delivery No significant differences between oral and intravenous administration of UCC2003 were observed in bacterial recovery (y axis) or luminescence (z axis) from s.c. tumours. UCC2003 cfu counts were similar on day 7 (p=0.360), with i.v. counts higher on day 11 (p=0.038) and oral counts higher on day 14 (p=0.021).

Figure 2:
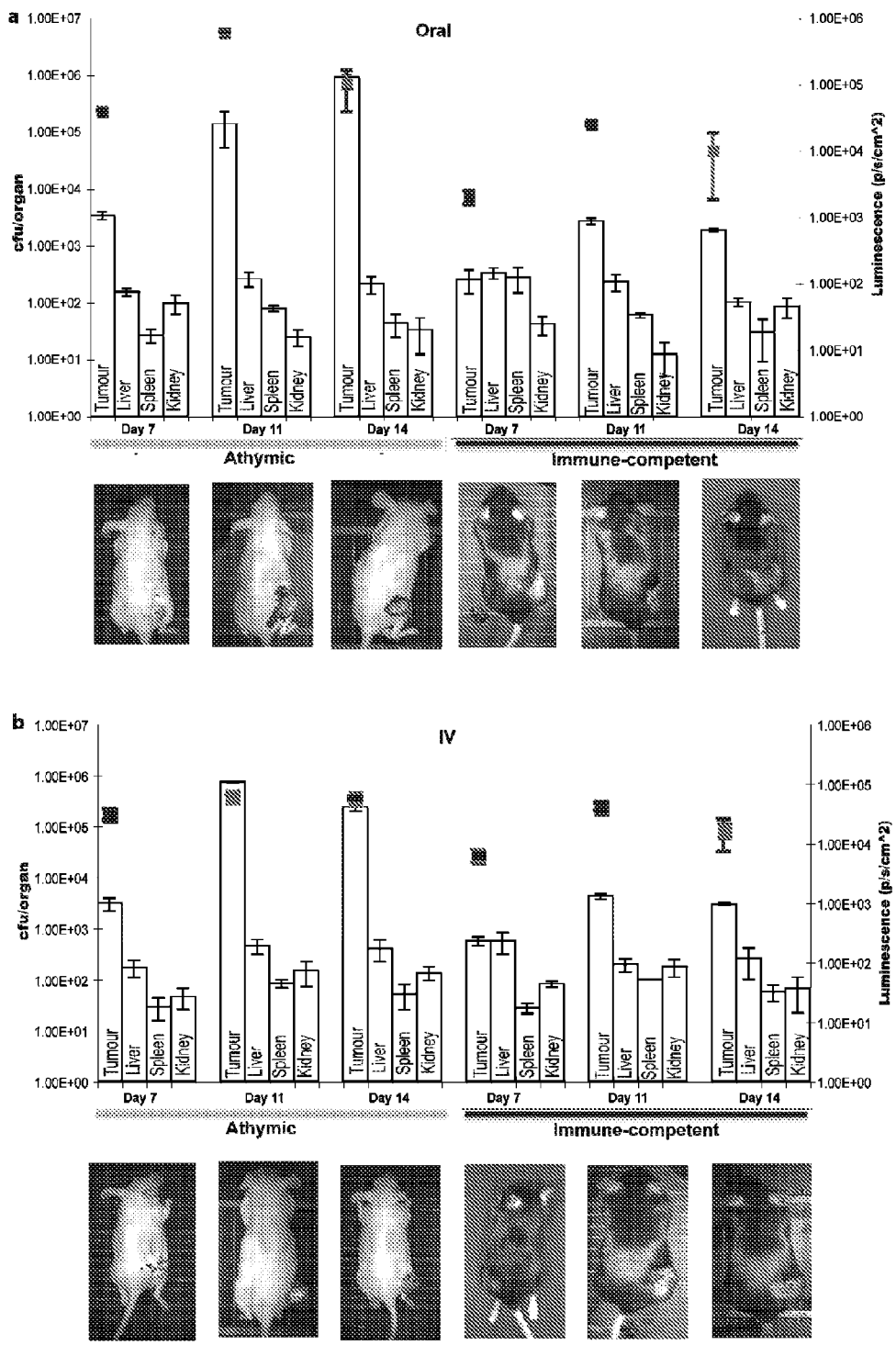

FIG. 2: Bifidobacterial translocation in immunocompetent mice UCC2003 recovery following either (a) oral or (b) intravenous delivery to athymic and immunocompetent mice. Bacterial recovery (y axis) and luminescence (z axis) from s.c. tumour tissue and various organs are represented. UCC2003 recovery from organs was comparable between both species and delivery mechanisms. Detectable luminescence and significantly higher bacterial recovery were observed in tumours of all mice relative to other tissues.

Figure 3:
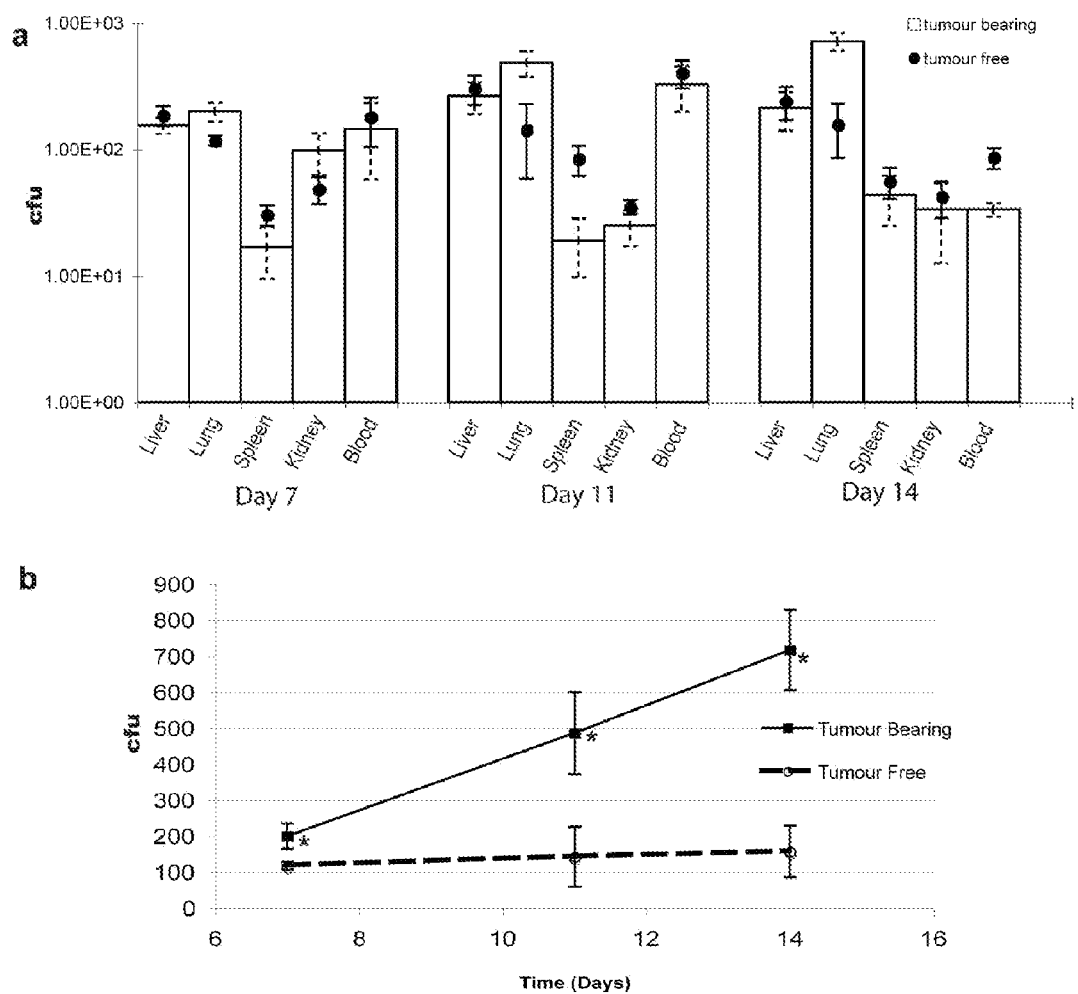

FIG. 3: Influence of tumour on systemic bifidobacterial spread Cfu levels in blood and organs were compared between tumour bearing and tumour-free mice orally administered UCC2003. (a) The presence of tumour did not significantly alter levels of cfu recovery from liver, kidney or blood (p>0.240). (b) Bacterial colonisation of B16 pulmonary metastases. Significantly increasing bacterial load was observed over time in lungs of tumour bearing animals (*Day 7 p=0.045, day 11 p=0.030, day 14 p=0.006) indicating bifidobacterial colonisation and replication in metastatic nodules.

Figure 4:
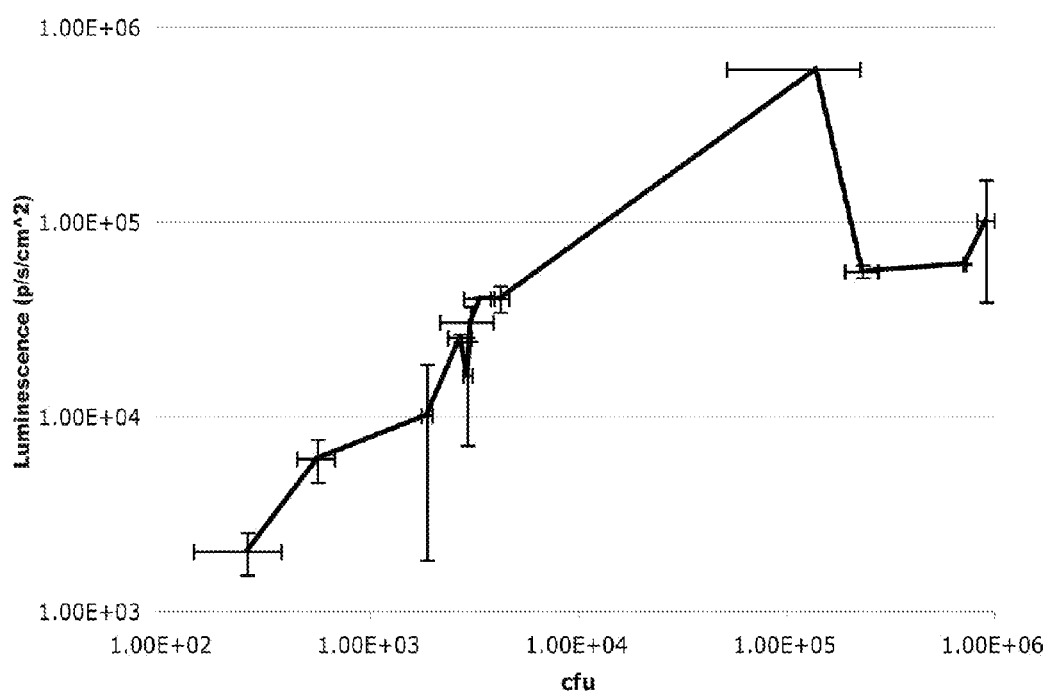

FIG. 4: Correlation between bacterial counts and luminescence

A linear relationship between luminescence and bacterial counts was observed up to $10^5$cfu. At higher bacterial load, luminescence underestimated. Since the activity of BioLuminescence Imaging systems are dependent on both ATP and oxygen availability [57, 58], lower luminescence (than expected based on bacterial cell counts) may be the result of decreased metabolic activity and/or reduced oxygen availability at higher bacterial concentrations and/or larger more hypoxic tumours. ATP, adensine triphosphate; cfu, colony forming units.

Figure 5:
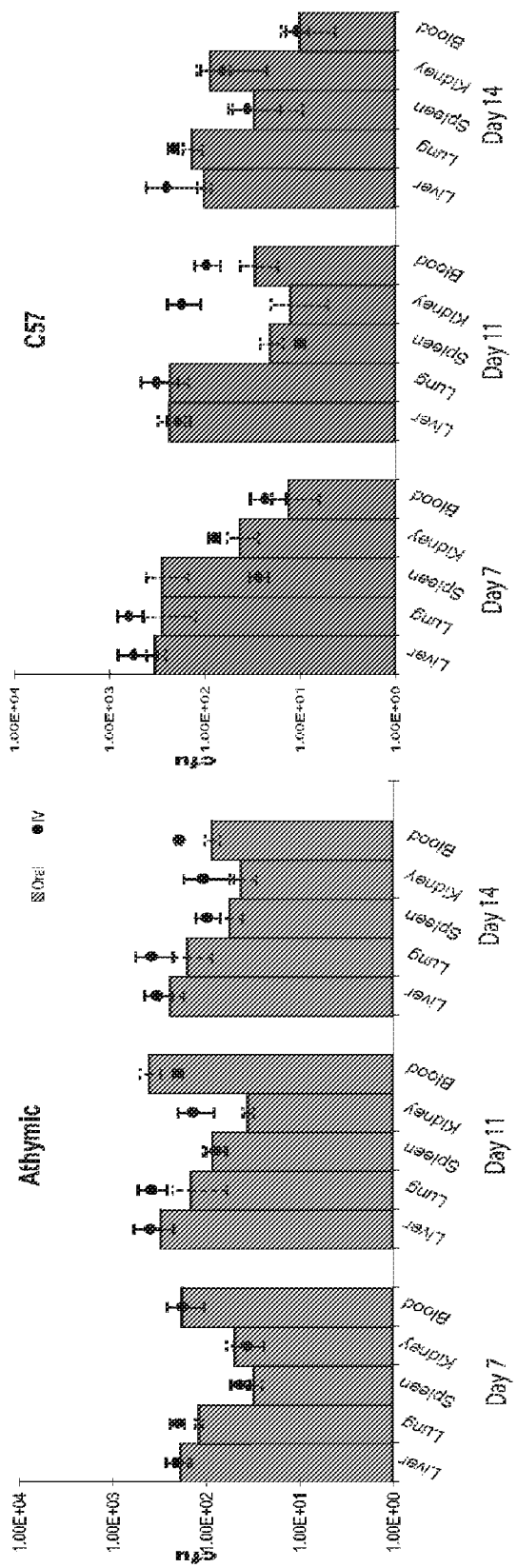

FIG. 5: Systemic localisation of UCC2003 administered orally or intravenously Bacterial counts in organs were compared between oral and i.v. administered tumour free athymic or immunocompetent C57 mice. Organ colonisation was similar in all cases.

Figure 6:
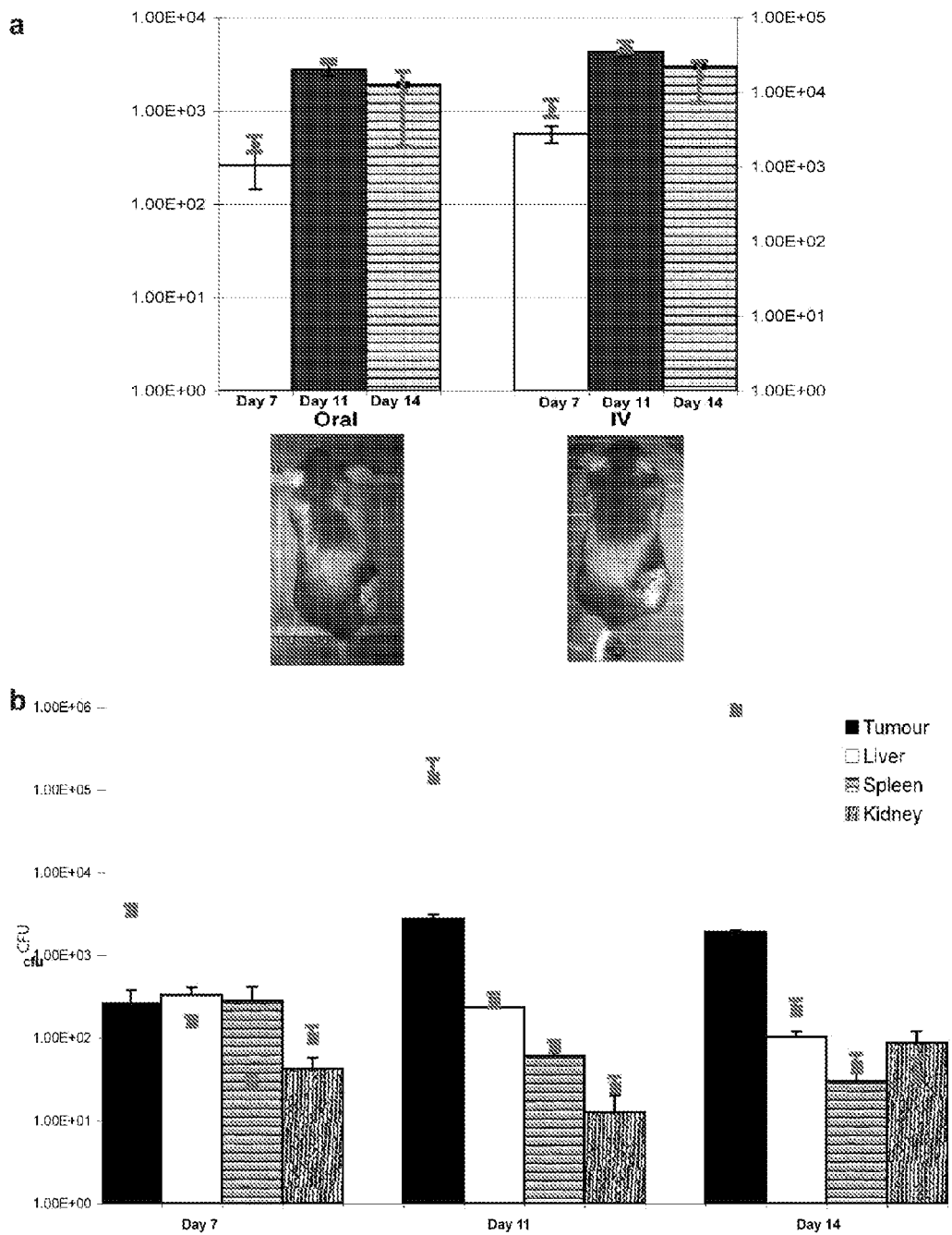

FIG. 6: Bifidobacterial translocation in immunocompetent mice (a) B. breve colonisation of tumours post oral or i.v. administration to immunocompetent animals. B. breve UCC2003 recovery (y axis) and luminescence (z axis) from B16-F10 tumours following either oral or intravenous delivery to immunocompetent C57 mice. Bacterial levels in tumours were comparable whether UCC2003 was orally or i.v administered. In all cases, detectable luminescence and significantly higher bacterial recovery (p<0.003) were observed in tumours relative to other tissues. Sample IVIS images from day 11 are shown.

(b) Comparison between B. breve levels in athymic and immune competent mice. Following oral administration of UCC2003, there were no significant differences (p>0.107) observed between cfu levels in organs from C57 mice (bars) and athymic mice (red dots). Tumour cfu levels were significantly higher in athymic mice, with differences of up to 3-log fold by day 14.

Figure 7:
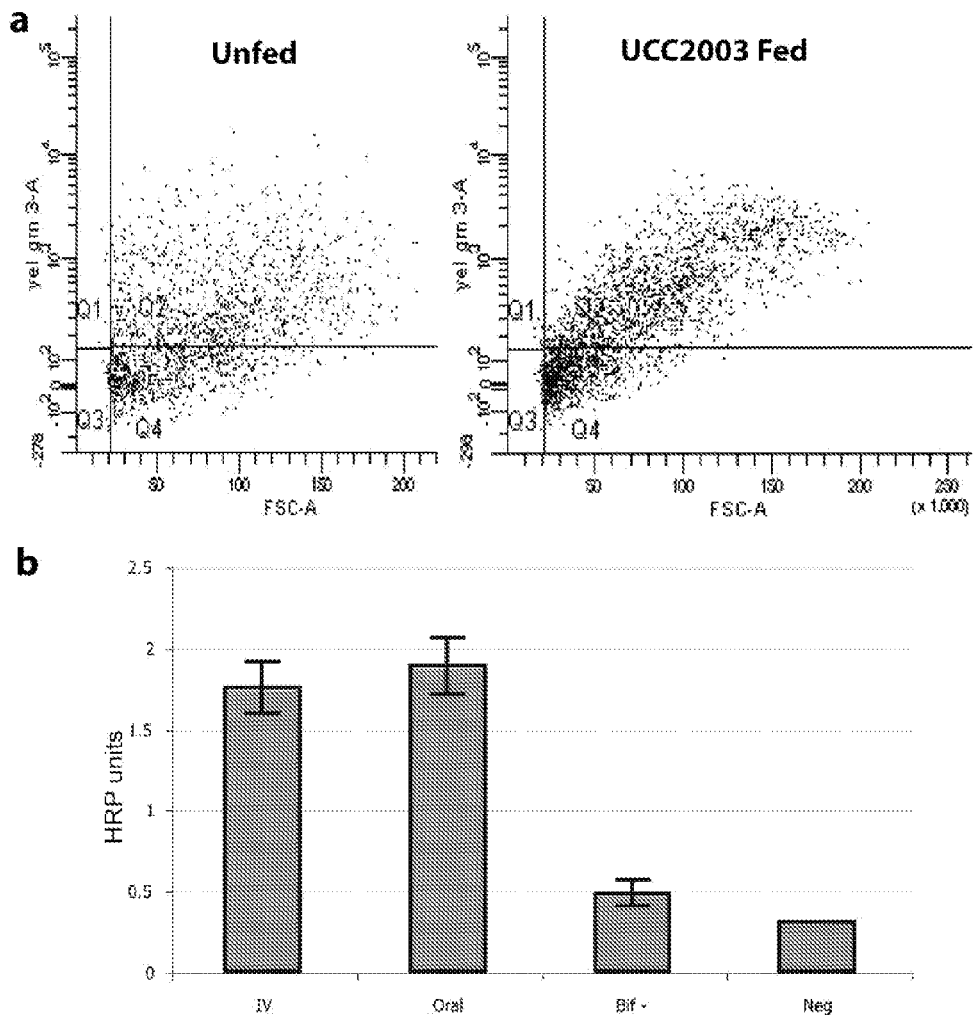
Figure 8:
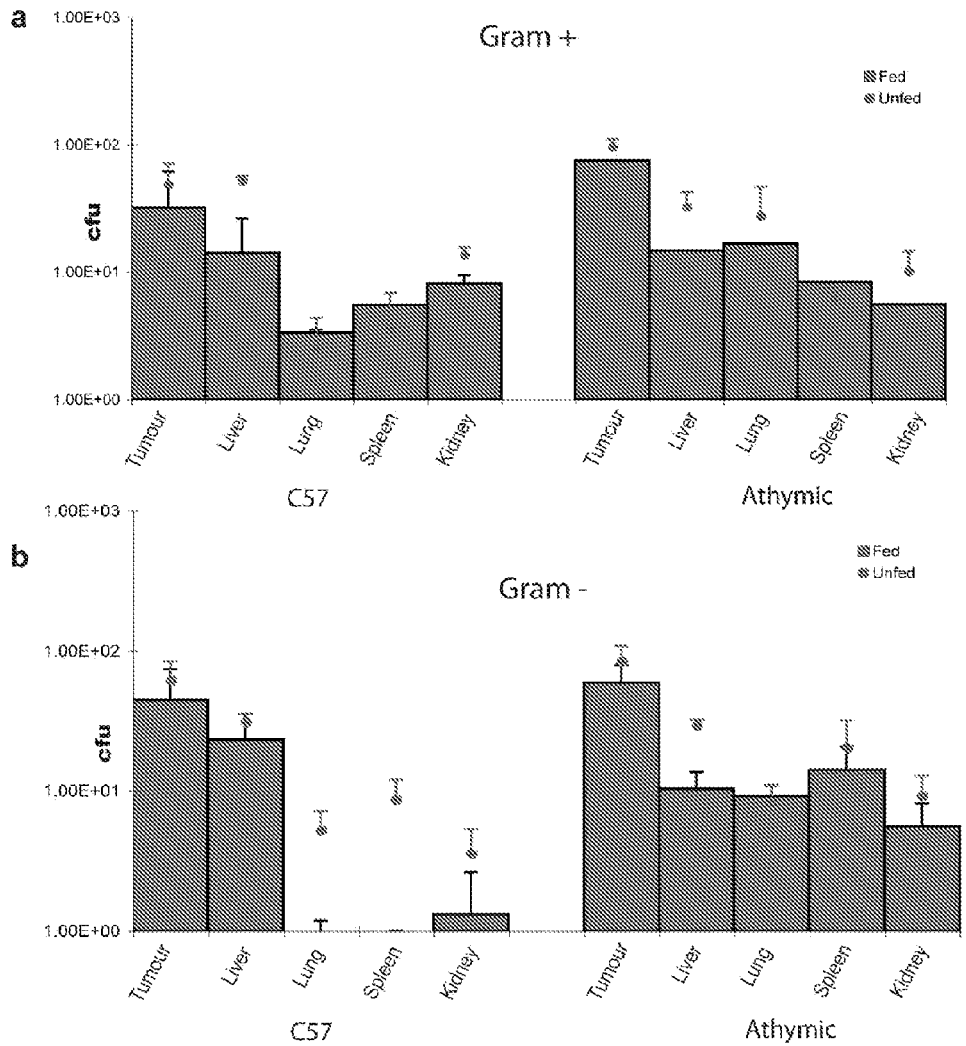

FIG. 7: Cellular and humoural immune responses to UCC2003
(a) T cell levels in bifidobacteria-colonised tumours. Flow Cytometry analysis was used to quantify CD3-positive T cells in s.c. tumours from C57 mice orally administered UCC2003 or PBS. A 25.8 (+/−5.8) % increase in total T cell numbers was observed in UCC2003 colonised tumours 11 days post feeding, compared with unfed mice (p=0.06, n=3).
(b) Humoural responses. IgG antibody specific for UCC2003 was measured by ELISA from serum taken from immunocompetent C57 mice 14 days post administration (n=3). Results indicated that antibodies were raised against UCC2003. There was no significant difference between anti-UCC2003 IgG antibody levels in serum from IV and fed mice (p=0.359). FIG. 8: Recovery of various bacterial genera from murine tissues
Low levels (5-50 cfu) of indigenous commensal bacteria (*Lactobacilli, Enterobacteriaceae, Staphlococci, Micrococci* and *Bacteroides*) were recovered from all organs examined, but not blood, in both immunocompetent and athymic mice. No differences in non-UCC2003 bacterial levels were observed between UCC2003-fed and control (PBS-fed) mice (p>0.114), except for decreases in Gram-negative bacteria in lung, liver and kidney of C57 mice fed UCC2003 (p<0.044), indicating inhibition of certain species by UCC2003.

DETAILED DESCRIPTION OF THE DRAWINGS

Materials and Methods
Cell Culture

*B. breve* UCC2003 (UCC Culture Collection) was routinely grown at 37.degree. C. in reinforced clostridial medium (RCM) (Oxoid, Basingstoke, United Kingdom). For bioluminescence assays MRS medium (Oxoid), supplemented with 0.05% (w/v) cysteine-HCl was used. Anaerobic conditions were maintained using an anaerobic chamber [Mac500, Don Whitley Scientific, West Yorkshire, UK (atmosphere 10% $H_2$, 10% $CO_2$, 80% $N_2$)]. *B. breve* UCC2003/pLuxMC3 [18], expressing the luxABCDE operon from the P.sub.help promoter [52] was cultured in the presence of 4.mu.g/mlchloramphenicol (Cm). To facilitate specific recovery of bifidobacteria from tissue samples, 50 mg mupirocin (Oxoid)/liter was included, as previously described [53]. B16-F10 (ATCC) was maintained in DMEM (GIBCO, Invitrogen Corp., Paisley, Scotland) supplemented with 10% FBS. Cell densities were determined by visual count using a haemocytometer and viable cell counts were conducted using trypan blue dye exclusion method (Gibco). 52. Riedel C U M I, Casey P G, Morrissey D, O'Sullivan G C, Tangney M, Hill C, Gahan C G. Improved luciferase tagging system for *Listeria monocytogenes* allows real-time monitoring in vivo and in vitro. Appl Environ Microbiol 2007; 2007;73:3091-3094. doi: 10.1128/AEM.02940-06. [PubMed].53. Simpson P J, Stanton C, Fitzgerald G F, Ross R P. Genomic diversity and relatedness of bifidobacteria isolated from a porcine cecum. J Bacteriol 2003; 185(8): 2571-2581.

Animals and Tumour induction

All in vivo experiments were approved by the ethics committee of University College Cork. For routine tumour induction, 1×10$^6$ B16-F10 tumour cells, suspended in 200 μl of serum-free DMEM (Sigma), were injected subcutaneously (s.c.) into the flank of 6-8 week old female C57 or MF1-nu/nu mice (Harlan, UK). Tumours were monitored mostly by alternate day measurements in two dimensions using a verniers calliper. Tumour volume was calculated according to the formula V¼ab2P/6, where a is the longest diameter of the tumour and b is the longest diameter perpendicular to diameter a.

Bacterial Administration

Figure 1:
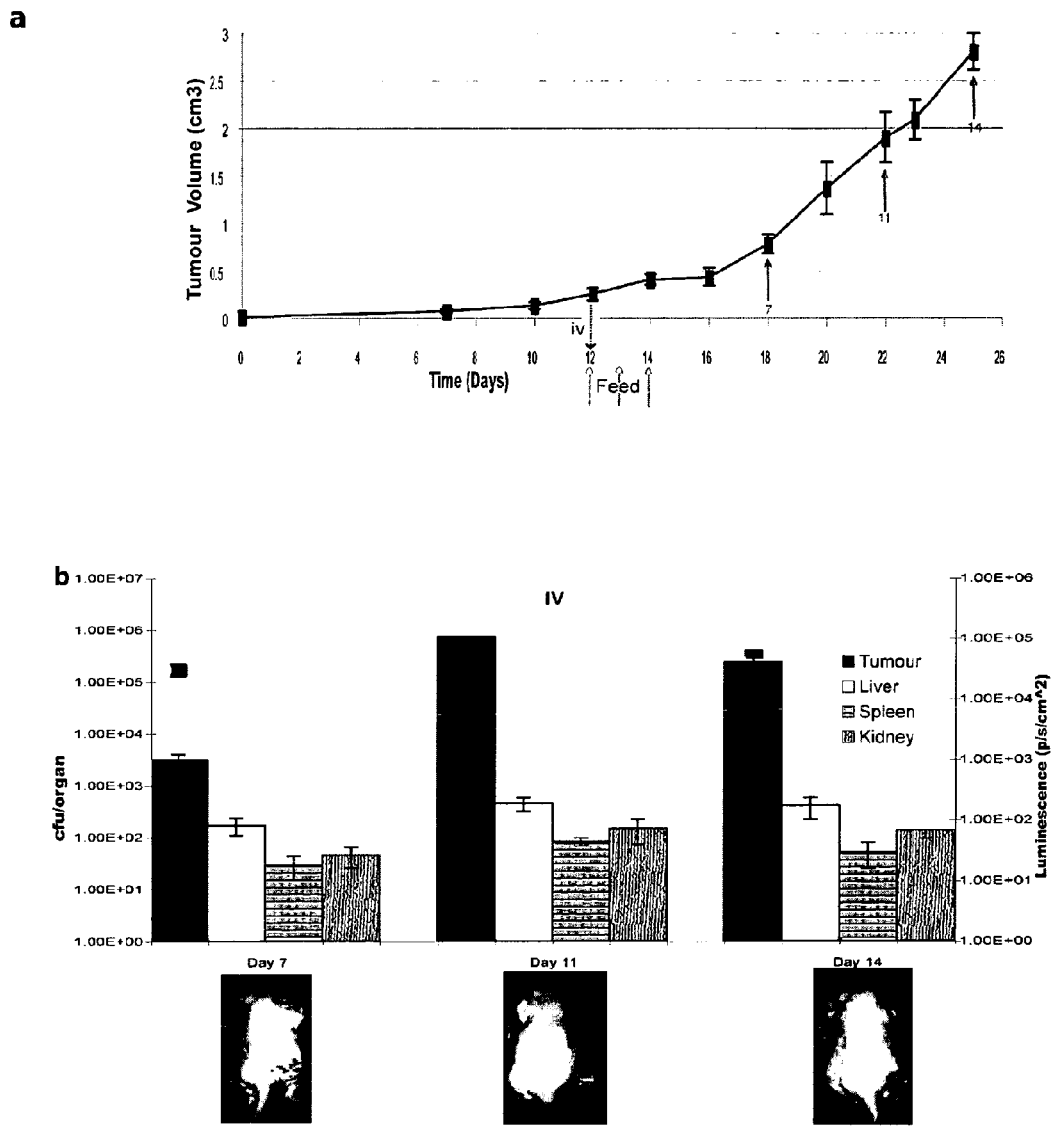
FIG. 1: (a) Protocol for animal trials Subcutaneous tumours were induced in mice, and bifidobacteria administered upon tumour development. For oral administration, each animal received $10^9$ B. breve UCC2003 on three consecutive days. For intravenous (i.v.) administration, each animal received $10^4$ cells injected directly into the lateral tail vein. Mice were imaged (IVIS) immediately prior to culling with subsequent recovery of viable bacteria (cfu) from tissues (arrows)
Figure 1:
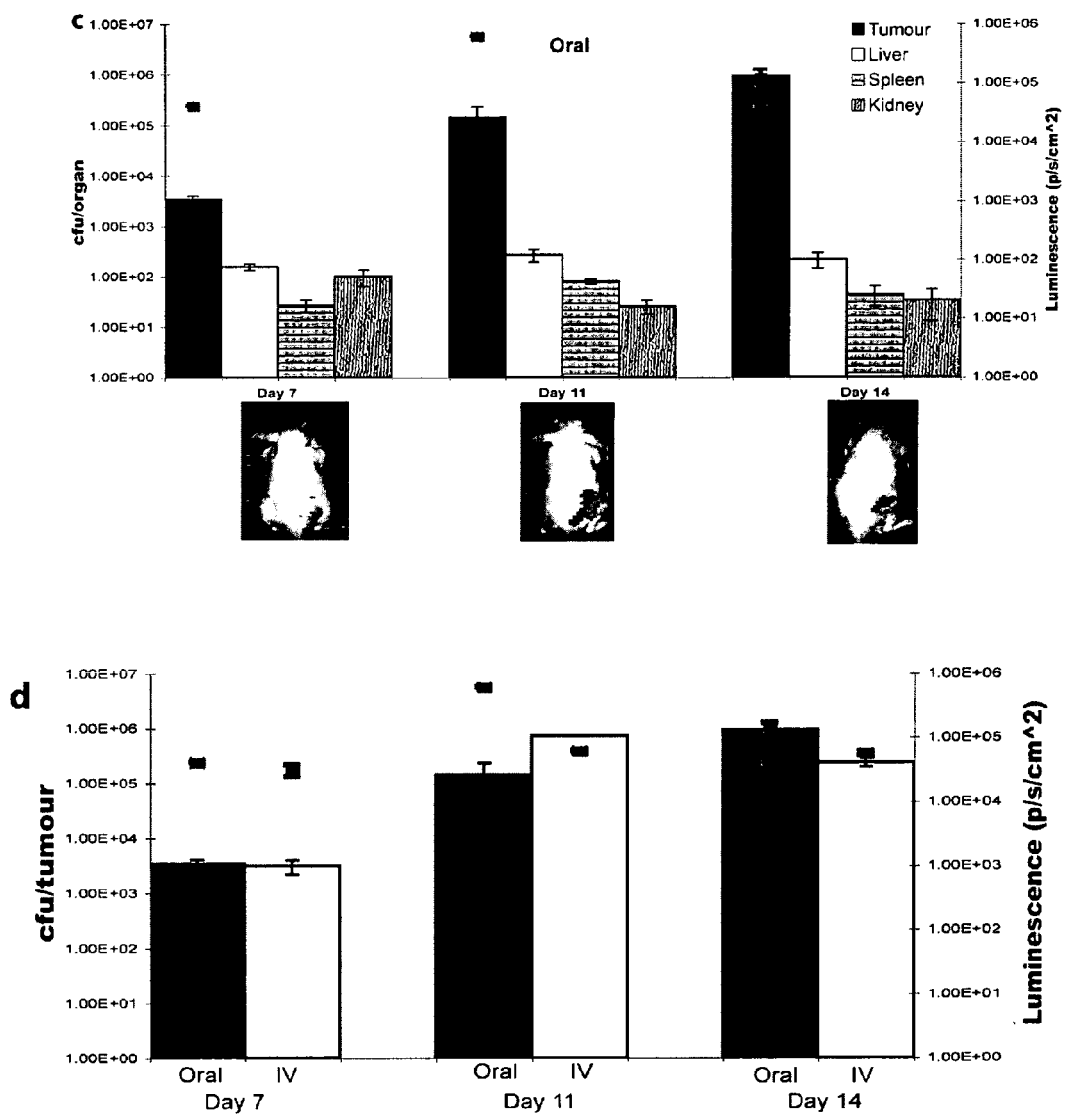

The inocula were prepared by growing *B. breve* UCC2003 containing pLuxMC3 anaerobically overnight at 37° C. in 100 ml of MRS broth containing 4 μg/ml Cm. Cultures were harvested by centrifugation (6,000×g for 5 min), washed with PBS supplemented with 0.05% cysteine HCl (Sigma), and resuspended in a one-tenth volume of PBS. When tumours reached approximately 100 mm$^3$ in volume, mice were randomly divided into experimental groups (n=6) and administered bifidobacteria or an equal volume of PBS as control. For oral administration, 10$^9$ cells was administered in 20 μl per mouse on three consecutive days using a micropipette tip placed immediately behind the incisors. For intravenous administration, each animal received 10$^4$ cells in 100 μl injected directly into the lateral tail vein, which we found to be the maximum injectable dose with this strain (FIG. 1). The viable count of each inoculum was determined by retrospective plating on Reinforced Clostridial Agar (RCA) containing 4 μg/ml Cm.

Whole Body Imaging

On day 7, 11 and 14-post first inoculation, animals were anesthetised by intraperitoneal administration of 200 mg xylazine and 2 mg ketamine, and whole-body image analysis was performed in the Xenogen IVIS 100 system for 5 minutes at high sensitivity.

Bacterial Recovery from Mice

Following imaging, a subset of animals from each group were euthanised by cervical dislocation. Cardiac puncture was immediately performed to obtain blood, and subsequently individual tumours as well as lungs, liver, spleen and kidneys were aseptically removed and examined for bioluminescence. Ex vivo IVIS imaging detected no luminescence in organs. Following imaging, each tissue was homogenized by fine mincing by scalpel followed by pushing through a 20 .mu.m pore nylon filter (FALCON, Becton Dickinson (BD), Oxford, England) in sterile PBS supplemented with 0.05% cysteine-HCl. Serial dilutions were plated in duplicate on RCA agar containing 4 .mu.g/ml Cm and mupirocin. Resulting colonies were used to calculate the number of UCC2003 cells per tissue sample. To confirm that cfu recovered were *B. breve*/pLuxMC3, random isolates were spot inoculated onto RCA only or RCA containing Cm 4 .mu.g/ml. Specific identification of UCC2003 pLuxMC3 was confirmed by PCR using primer pairs targeting both the intergenic spacer region and the unique apuB gene on the chromosome of UCC2003 (5'-GGTGTGAAAGTCCATCGCT-3' and (SEQ ID NO: 1)5'-GTCTGCCAAGGCATCCACCA-3'(SEQ ID NO: 2)).sup.19.

To facilitate the recovery of other bacteria potentially translocating from the GIT, total tissue homogenates were serially diluted and plated on MRS agar (Oxoid) to select for aerobic Gram-positive bacteria and on McConkey agar (Oxoid) to select for Gram-negative bacteria. Plates were incubated for 24-48 h and cfu enumerated. Morphology of differing colony types was assessed and the colonies re-streaked. Following catalase and Gram reaction tests, five colony types were subjected to API analysis (BioMerieux) to determine species.

DNA Extraction and Auantitative PCR

Tumours (average volume 1 cm$^3$) were excised from MF1 nu/nu mice 11 days post oral administration of UCC2003/ pLuxMC3. Each tumour was aseptically dissected to separate the periphery from the central region. Necrosis was evident in the centre of tumours of this size. Total DNA was extracted from each segment using the Sigma GenElute DNA extraction kit with the following modifications; DNA samples were flash frozen in liquid nitrogen and homogenised; digestion of the tissue was in lysis buffer containing 40 mg/ml proteinase K and incubation was increased to overnight at 55° C. As a UCC2003-free control, DNA was also extracted from the tumour of a naive mouse. The concentration of DNA in all samples was determined using the Nanodrop system (ND-1000 Spectrophotometer, Labtech Int, East Sussex, UK), and equal concentrations of DNA added to each PCR reaction. The concentration of the mammalian cell housekeeping gene Glyceraldehyde-3-phosphate dehydrogenase (GAPDH) was also determined for all samples to ensure parity between PCR template DNA samples. Quantitative PCR (qPCR) was performed using the LightCycler system (Roche Diagnostics, U.K.). A 20 μl reaction contained 0.5 μM of each sense and anti-sense primer, 4 mM $MgCl_2$, 2 μl LightCycler FastStart DNA Master SYBR Green and 100 ng of template DNA. PCR conditions were 95° C. for 10 min; 95° C. for 10 s, 56° C. for 5 s for luxA primers (59° C. for GAPDH primers), 72° C. for 5 s. Melting curve: 95° C. for Os, 66° C. for 15 s, 99° C. for 0 s; Cooling step: 40° C. for 30 s. The concentration of pLuxMC3 in each sample was determined using a standard curve generated with pLuxMC3 plasmid DNA, and corresponding plasmid copy number calculated using the formula (Mass DNA/ug=n by plasmid/$3 \times 10^9$ bp). pLuxMC3 has an average copy number/cell of 3±0.18 in UCC2003, and resulting plasmid copy numbers were divided by this figure to calculate bacterial cell numbers/μg DNA.

Flow Cytometry Analysis

Mouse tumours were excised and finely minced using a scalpel. Tissue was subsequently chemically dissociated in DMEM containing Collagenase I (300 U/ml, Sigma Aldrich) and DNase (0.01%, Sigma Aldrich) for 40 min at 37° C. and then applied to a cell strainer (70 μm mesh size, Becton Dickinson, UK). Red blood cells were lysed using ACK erythrocyte lysis buffer (distilled H2O, 0.15 M NH4Cl, 10 mM KHC03, 0.1 mM Na2EDTA) and cell counts determined using a NucleoCounter (Chemometec, Denmark). Cells at a concentration of $1 \times 10^6$ cells per 100 μl were washed in PBS and fixed using 70% ethanol. FACS analysis was performed using anti-mouse CD3e-PE-Cy5 (145-2C11), anti-mouse Fc block (CD16/32) and relevant isotype control as per manufacturer instructions (eBioscience, USA). FACS staining buffer (PBS, 2% FBS, 1% BSA and 0.05% sodium azide) was used as wash and staining buffer. Analysis was performed on a FACSDiva (BD, England) and analysed using BD FACS-Diva software 6.0 (BD, England).

Antibody Detection

Antibody was measured by an indirect-Enzyme Linked ImmunoSorbent Assay (ELISA), as described in Yasui et al. [56] with the following modifications. B. breve UCC2003 cells ($1.times.10.sup.8$ bacteria/well) were coated on the wells of a 96-well ELISA plate using carbonate buffer pH 9.6 and incubated at room temperature (RT) overnight. Blood samples were collected at necropsy by cardiac puncture from female C57 BL/6 mice administered UCC2003 either orally (n=3) or intravenously (n=3), or untreated mice (n=3), as previously described. To separate plasma, the samples were centrifuged for 10 minutes at 4000.times.g within 30 minutes of collection. Plates were blocked for 1 hour at 37.degree. C. by the addition of 10% rabbit serum diluted in PBS containing 0.05% NaN3 (PBSN). After washing three times with PBSN, 50 .mu.l of mouse serum samples (1:1,1:10, 1:100 dilutions) in blocking buffer (0.05% TWEEN® 20 and 0.25% BSA in PBSN) were added to the plates and incubated overnight at RT. All samples were assayed in triplicate. The plates were then blocked again by 1 hour incubation at 37.degree. C. in 10% sheep serum, and further incubated with goat anti-mouse IgG conjugated to alkaline phosphatase (Sigma) for 5 hours at RT. After incubation with the substrate pNPP, qualitative hydrolysis of NPP was detected using a microtiter plate reader (VMAX, Molecular Devices) with a 405-nm filter. Antibody levels are expressed as the means and standard error of the values for three mice per route. 56. Yasui H, Mike A, Ohwaki M Immunogenicity of *Bifidobacterium breve* and change in antibody production in Peyer's patches after oral administration. *J Dairy Sci* 1989; 72(1): 30-35.

Cytokine Analysis

MF1nu/nu mice bearing B16 tumours were sacrificed by cervical dislocation at 11 days post-feeding with *B. breve* UCC2003 pLuxMC3 or PBS. The blood samples were obtained using cardiac puncture, serum separated by centrifugation and used immediately for the cytokine assay. The entire GIT was also extracted, frozen and then homogenised on ice in tissue lysis buffer containing a denaturing detergent (<0.1% SDS) and reducing agent (<1 mM DTT) as well as 1% BSA. The MSD Murine Cytokine 7-plex ultrasensitive panel (Meso Scale Discovery, Gaithersburg, Md., USA) was run as per kit recommendations. This plate analyses murine Interferon-gamma (IFN-γ), Interleukin-1 beta (IL-1b), Interleukin-6 (IL-6), Interleukin-10 (IL-10), Interleukin 12 (IL-12p70), Tumor necrosis factor (TNF-α and the mouse keratinocyte-derived chemokine (mKC), a functional homolog of human interleukin-8.

Statistical Analysis

Two-tailed Student's t-tests were employed to investigate statistical differences. Microsoft Excel 12 (Microsoft) was used to manage and analyze data. Statistical significance was defined at the standard 5% level.

Results

In vivo Imaging of Bifidobacteria in Tumours

The inventors administered *B. breve* UCC2003 carrying the plasmid pLuxMC3, which expresses the luminescent bacterial luxABCDE operon under the control of the bacterial $P_{help}$ promoter, by tail vein injection to athymic MF1 nu/nu mice bearing subcutaneous (s.c.) B16-F10 murine melanoma tumours (FIG. 1).

Bacterial luminescence was readily detected specifically in s.c. tumours by live whole body imaging (IVIS) (FIG. 1b). Ex vivo bacterial quantification by culture of tumours and other organs showed presence of UCC2003 in all tissues examined, indicating migration of *B. breve* from the GIT and systemic spread to internal tissues. Numbers of UCC2003 were low in organs, ≤100 colony forming units (cfu)/organ, relative to the bacterial numbers present in tumour, and decreased over time. In contrast, high-level replication was observed in tumours, reaching cfu levels of $10^6$/tumour by day 14 (FIG. 1b). Tumour volume curves indicated no significant difference in tumour growth rates between bifidobacterial administered mice and controls (data not shown). Live imaging of luminescence from lux-expressing bifidobacteria provided a robust system for indication of bacterial numbers in tumour masses as well as providing evidence of plasmid gene expression (FIG. 4).

*B. breve* UCC2003 Translocates from the GIT and Colonises Tumours when Administered Orally at Levels Equal to I.V. Administration.

Previous studies have reported bacterial localisation to tumours only following intravenous administration. When intravenous administration of this strain was examined, similar results were observed (FIG. 1c), with no significant differences in colonisation levels between oral and iv administration in tumours or other tissues (FIG. 1d, FIG. 5), indicating that oral administration is as effective in achieving targeted tumour growth as the well described intravenous route, using our optimised protocols.

Comparisons indicated that oral administration was as effective in achieving targeted tumour-located growth as the well-described i.v. route, using our optimised protocols, and indeed, maximum tumour cfu levels were observed with orally administered mice, on day 14 (FIG. 1d). No significant differences were observed between oral and i.v administration in organs (p>0.058) (FIG. 5). In order to establish that the phenomenon was not tumour-type specific, the inventors repeated the study in MF1 nu/nu mice bearing s.c. MCF7 human breast tumour xenografts or C57 mice bearing s.c. Lewis Lung Carcinoma tumours and observed similar results.

Pattern of *B. breve* UCC2003 Growth within Tumours

UCC2003 levels within central or peripheral regions of subcutaneous tumours were assessed utilising quantitative PCR (specific for lux) on total DNA isolated from tissue taken from either the periphery or centre of 1 cm$^3$ tumours resected from athymic mice 11 days post feeding. Vector was detectable only in the central region, at $7.28 \times 10^8$ ($\pm 1.87 \times 10^7$) bacterial cells/µg total DNA, suggesting preferential growth within anaerobic regions (data not shown). The B16 tumour model spontaneously metastasises from s.c. tumours to lungs. Significantly increasing bacterial load was observed over time in lungs of tumour bearing athymic mice fed UCC2003 (p<0.045), indicating bifidobacterial colonisation and replication in small (potentially pre-hypoxic) metastatic nodules (FIG. 3(b)). No increase in luminescence was observed, suggesting these bacterial levels were below the luminescence detection limit Route of Trafficking is Via Serum UCC2003 was recovered from serum and not the cellular component of blood up to day 14 post feeding (FIG. 5), indicating haematogenous trafficking of free bacteria from the GIT. *B. breve* numbers in blood were similar at all time points whether administered i.v. or orally.

Translocation does not Require Presence of Tumour

When cfu levels in blood and organs were compared between tumour-bearing and tumour-free mice, no significant differences were observed for liver, kidney and blood (p>0.240) (FIG. 3a), indicating that translocation is not mediated or promoted by some tumour-related factor. The B16 tumour model spontaneously metastasises from s.c. tumours to lungs. Significantly increasing bacterial load was observed over time in lungs of tumour bearing athymic mice (p<0.045), indicating bifidobacterial colonisation and replication in metastatic nodules. No increase in luminescence was observed, suggesting these bacterial levels were below the luminescence detection limit Nonetheless, live imaging of luminescence from lux expressing bifidobacteria provided a robust system for indication of bacterial numbers in larger tumour masses as well as providing evidence of plasmid gene expression (FIG. 3b).

Immune Responses to Vector

Comparison between bacterial levels in athymic and immunocompetent C57 mice indicated the involvement of T cells in bifidobacterial containment in tumours, while translocation to organs occurred at similar levels (p>0.107) (FIG. 6). UCC2003 levels in tumours were significantly increased specifically in tumours in the absence of T cells, with both oral and i.v. administration. To investigate the effect of UCC2003 on T cell levels in tumours, flow cytometry analysis was used to quantify CD3-positive T cells in s.c. tumours from C57 mice orally administered UCC2003 or PBS (FIG. 7). A 25.8 (+/−5.8) % increase in total T cell numbers was observed in UCC2003 colonised tumours 11 days post feeding, compared with unfed mice (p=0.06, n=3). Nonetheless, even in immunocompetent animals, bacteria were readily detected by IVIS imaging specifically in tumours at levels comparable to i.v. administration (FIG. 6(a)). The finding that organ cfu levels were not higher in athymic mice suggests that T cells do not inhibit translocation of bifidobacteria, but do significantly inhibit tumour-associated replication locally.

UCC2003 was found to persist indefinitely in athymic mice (up to 40 cfu/organ and 5 cfu/ml blood at week 5-post feeding) but was eventually cleared in immunocompetent animals by week 5-post oral administration (data not shown), indicating immune recognition by T cells but the ability to evade other immune effector systems. IgG antibody specific for UCC2003 was detected by ELISA in serum taken from immune-competent C57 mice 14 days post administration (FIG. 6b). There was no significant difference between anti-UCC2003 IgG antibody levels in serum from IV and fed mice (p=0.359). Circulating levels of cytokines examined were not significantly increased in serum from fed mice, except for the proinflammatory cytokine IL1β (946.16 ±47.31% with respect to unfed mice levels, p<0.001), suggesting the presence of some, but not a dramatic, degree of immune inflammatory response to systemic UCC2003 cells (data not shown).

Examination of Mechanism of Gastrointestinal Egress

Increased levels of cytokines such as IFNγ in the GIT are associated with increases in epithelial permeability and gut barrier loss in pathogenic bacterial sepsis [19, 20]. Non-pathogenic bacteria have previously been shown to upregulate cytokines such as IFNγ and IL12 in the GIT [21, 22]. In our experiments, cytokine analyses of IFNγ, IL1b, IL12p70, IL6, IL10, TNFα and KC levels were performed on GIT samples from UCC2003-fed and PBS-fed B16 tumour bearing athymic mice. Only IFNγ levels differed between the groups, with UCC2003 colonised GIT samples found to have significantly higher levels of this cytokine (295±44%, p=0.003), with respect to unfed mice, suggesting a possible IFNγ induced increase in epithelial permeability.

In order to examine for the possibility that UCC2003 feeding might result in generic increased translocation of GIT-residing bacteria, we compared systemic bacterial levels between UCC2003 fed and PBS fed mice. Low levels (5-50 cfu) of indigenous commensal bacteria (subsequently identified as *lactobacilli, enterobacteriaceae, staphlococci, micrococci* and *Bacteroides* by API analysis) were recovered from all organs examined, but not blood, in both immunocompetent and athymic mice (FIG. 8). No differences in non-UCC2003 bacterial levels were observed between UCC2003-fed and control (PBS-fed) mice (p>0.114), except for decreases in Gram-negative bacteria in lung, liver and kidney of C57 mice fed UCC2003 (p<0.044), indicating inhibition of certain species. These data suggest that UCC2003 specifically mediates its own translocation, with no collateral translocation of other commensal bacteria. To examine the route of bacterial trafficking from the GIT, various fractions of whole blood were assessed for presence of *B. breve*. Up to 500 cfu/ml UCC2003 were recovered from serum and not the cellular component of blood, when examined up to day 14 post feeding, indicating haematogenous trafficking of free bacteria from the GIT, rather than immune cell-mediated phagocytosis and transport. Orally administered *B. breve* numbers in blood remained static over this 14-day period, and were similar to i.v. levels at day 7 (p=0.296), while i.v. UCC2003 numbers decreased over time.

We also assessed if the presence of a tumour was required for bacterial translocation to occur. When cfu levels in blood and organs were compared between tumour-bearing and tumour-free mice, no significant differences were observed for liver, kidney and blood (p>0.240) (FIG. 3(a)), indicating that translocation is not mediated or promoted by some tumour-related factor.

B. breve Colonisaton of and Replication in Tumours is Increased Specifically in Tumours in the Absence of T Cells, with both Oral and i.v. Administration.

Comparison between bacterial levels in athymic and immunocompetent C57 mice indicated the involvement of T cells in bifidobacterial containment in tumours, while translocation to organs occurred at similar levels (p>0.107) (FIG. 2). UCC2003 levels in tumours were significantly increased specifically in tumours in the absence of T cells, with both oral and i.v. administration (FIG. 2). Nonetheless, even in immunocompetent animals, bacteria were detected by IVIS imaging specifically in tumours, indicating the potential for this strategy of tumour detection or treatment. The finding that organ cfu levels were not higher in athymic mice suggests that T cells do not inhibit translocation of bifidobacteria, but do significantly inhibit tumour-associated replication locally.

Discussion

The inventors have shown for the first time that a food grade bacterial vector can be ingested, resulting in high-level gene expression over time in systemic tumours. The inventors have further developed an imaging system for bifidobacteria, which permits their detection in tumours, and consequently the detection of tumours, in real time by luminescence imaging. The nature of the bacterial lux system is such that no exogenous substrate is required for detection. Luminescence is largely un-investigated at clinical level, as mammalian luminescence reporter genes such as firefly luciferase require additional chemical substrates for function, which are not licensed for clinical use. Thus, the use of bacteria expressing lux in tumours presents a potentially powerful diagnostic clinical tool. Furthermore, this bacterial vector could be engineered to express alternative genes for use with existing clinical diagnostic equipment, such as HSV thymidine kinase in combination with positron emission tomography (PET) [23]. UCC2003 preferentially colonises the caecum, with peak levels of $10^6$ cfu/g tissue observed 19 days post feeding, and $10^5$ cfu/g tissue one month post feed [18]. It is unlikely that increasing tumour bacterial load over time is due to newly translocated bacteria becoming trapped in tumour microvasculature, as bacterial levels also increased in tumours in i.v. administered mice receiving a single dose of UCC2003. The precise mechanism of tumour-specific bacterial growth has yet to be demonstrated. Several groups have demonstrated homing to and replication in tumours, with many types of bacteria, including bifidobacteria, following i.v. injection [1-3,5]. Early observations with strictly anaerobic bacteria (clostridia and bifidobacteria) lead to the hypothesis that, unlike normal tissues, the hypoxic environment in tumours provides anaerobic growth conditions [24,25]. However, evidence of similar tumour-specific growth of non-anaerobic bacteria, coupled with findings of growth in small, pre-hypoxic tumours, suggest that lack of oxygen in the necrotic centre of tumours may not be the determining factor for the tumour specific nature of bacterial growth in theses settings [5]. In the inventors' studies, B. breve UCC2003 was observed to increase over time in lungs containing small (<5 mm$^3$) B16 pulmonary metastatic nodules, also suggesting that hypoxia may not be a requirement for anaerobic bacterial targeting. Yu et al proposed that the entry, survival and replication of bacteria in tumours is dependent on tumour vascularisation and the tumour immune microenvironment which provides a sanctuary for a small number of bacteria that will escape the immune system [5]. This model involves bacteria entering the tumour's leaky vasculature and escaping the host immunosurveillance due to the immune-privileged nature of solid tumours. Tumour cell line xenografts are known to have different vasculature to spontaneously arising tumours, and investigations in an appropriate spontaneous tumour murine model may yield more clinically relevant data. The nutrient rich environment may also play an important role as evidenced by findings that tumours can support the replication of auxotrophic strains of S. typhimurium [26, 6, 27]. The nature of growth within tumours also appears to be bacterial strain specific. It has been reported for many species, including strains of S. typhimurium, that the bacterial vector growth was confined to the central necrotic regions of tumours while in contrast, the S. typhimurium A1 strain has been shown to grew throughout the tumour, including viable malignant tissue in a wide range of tumour models [28, 29, 26, 30, 6, 27]. In the inventors' studies, UCC2003 was detected solely in the central necrotic region.

The inventors report that UCC2003 persisted indefinitely in athymic mice but was eventually cleared in immunocompetent animals indicating immune recognition by T cells but the ability to evade other immune effector systems. It is noteworthy that bacterial replication was restricted in immunecompetent mice specifically in tumours. It is likely that these anti-UCC2003 immune responses are active systemically, but a reduction in organ numbers as evidence by the inventors' assays may be masked by the constant influx of newly translocated bacteria, while tumour located bacteria do not exponentially multiply at the same rate in tumours in immunecompetent as in athymic mice, resulting in readily measurable differences. The absence of significant up-regulation of cytokines characteristic of anti-bacterial responses in blood further demonstrated immune tolerance to this strain. Previous studies in cynomolgus monkeys, dogs and guinea pigs have indicated no adverse effects following intravenous administration of *Bifidobacterium longum* [31]. Recent reports indicated differential stimulation of the immune system by bifidobacteria depending on species, and indeed strain, with *B. breve* shown to have little effect on the immune system, while specific *B. longum* strains influenced the orientation of Th1/Th2 responses differently [32].

31. Fujimori M. Genetically engineered *bifidobacterium* as a drug delivery system for systemic therapy of metastatic breast cancer patients. *Breast Cancer* 2006; 13(1): 27-31.

Fu et al previously described the use of *B. longum* to deliver a therapeutic peptide to the GIT [33]. In that report, *B. longum* expressing endostatin was administered orally to athymic mice, and the authors reported that subsequent gut absorption of the therapeutic peptide resulted in slowing in the growth of s.c. liver tumours. Translocation of bacteria from the gut to tumours was not investigated or reported in that study. The current inventors demonstrated that *B. breve* UCC2003 survives the upper GIT, colonises the caecum and translocates to extra-intestinal sites. Most bacteria which breach the epithelial barrier are killed by gut-associated lymphoid tissue [14]. In healthy animal models in which the intestinal barrier is not physically damaged, indigenous bacteria have been shown to translocate by an intracellular route through the epithelial cells lining the intestines and then travel via the lymph to the Mesenteric Lymph Nodes [34, 35]. The inventors' data suggest that immune cell uptake or transport was not involved in UCC2003 trafficking as all *B. breve* bacteria in blood were found in serum only. In animal models exhibiting damage to the mucosal epithelium, indigenous bacteria translocate intercellularly between the epithelial cells to directly access the blood [15]. Most bacteria, which breach the epithelial barrier, are killed by the gut-associated lymphoid tissue GALT [33]. It is unknown why UCC2003 was tolerated by the immune system in these studies. It was found that this bacterium persisted indefinitely in athymic mice (up to 40 cfu/organ and 5 cfu/ml blood at week 5; data not shown) but was eventually cleared in immunocompetent animals by week 5-post oral administration, indicating immune recognition by T cells but the ability to evade other immune effector systems. Findings of 1000 times increase in tumour associated bacterial levels in the absence of T cells presents the potential for improvement of this strategy via temporary local manipulation of T cells.

The ability of microorganisms to translocate, survive, and proliferate in extra-intestinal tissues involves complex interactions between the host defence mechanisms and the bacterium's ability to invade host tissues. Although the importance of host immune function [36, 37, 34] and the bacterium's intestinal population size [38, 39, 34, 40, 41] have been implicated as significant contributory factors, the precise mechanisms involved remains unknown [42, 43].

It is unlikely that increasing tumour bacterial load over time is due to newly translocated bacteria becoming trapped in tumour microvasculature, as bacterial levels also increased in tumours in i.v. administered mice receiving a single dose of UCC2003.

While significant evidence for the translocation of pathogenic bacteria exists [44, 45], relatively little information is available on translocation by indigenous species. In animal models, the recovery of *Bacteriodes, lactobacilli* and *enterococci* has been reported in healthy pathogen-free mice [46, 15, 38, 39], and Yamazaki et al. also reported *B. longum* colonisation of organs post feeding [47]. Sampling from humans has indicated that bacterial translocation may be a phenomenon that occurs in healthy individuals and may be a normal physiological event without deleterious consequences [48]. Clinical studies with probiotic bacteria conducted with healthy subjects have not reported severe disease caused by the bacteria even when shown to translocate from the gastrointestinal tract [42]. *Lactobacillus, Leuconostoc, Pediococcus, Enterococcus*, and *Bifidobacterium* have been isolated from infected lesions in patients [42, 49-51]. Penn et al. [34] reported an increased translocation from the GIT of S-180 tumour-bearing mice, leading to the hypothesis that immune deficiencies associated with progressive tumour growth may be sufficient to permit viable bacteria to translocate from the GIT. The inventorse did not observe statistically significant differences in Gram-negative or Gram-positive organ bacterial levels between B16 tumour-bearing and -free athymic or C57 mice, and the presence of tumour was not necessary for UCC2003 translocation to systemic organs to occur. *Food Chem Toxicol* 2000; 38(2-3): 153-161.

The population level obtained in the GIT by a particular bacterial species may be a critical factor determining whether or not this bacterial species will translocate to other organs [38]. This has been observed for *E. coli* in the presence of an intact anaerobic flora, where caecal concentrations of greater than $10^7$ *E. coli* per gram are required before this organism reliably translocates to other sites in healthy mice [39-41]. The inventors' cytokine analyses indicated that UCC2003 colonisation altered the local GIT cytokine milieu, perhaps leading to an IFNγ-induced increase in epithelial permeability. Examination of other commensal bacteria indicate that rather than *B. breve* inducing a general leakiness of the GIT barrier permitting generic bacterial translocation, UCC2003 specifically mediates its own translocation, with no collateral translocation of other commensal bacteria.

The *B. breve* UCC2003 translocated bacteria proved non-pathogenic even in immunocompromised animals and if desired the vector could be easily cleared systemically by antibiotic administration. The current inventors have shown that ingestion of these non-pathogenic bacteria carrying a gene of interest, in this case a luminescent reporter, results in high-level expression specifically in tumours. Since up to $10^6$ bacterial cells (with multiple plasmid gene copies/cell) were recovered from tumours, the potential for efficient delivery of genes to the tumour environment compares favourably with existing vectors. The current inventors have shown that bifidobacteria survive the upper GIT, colonise the caecum and translocate, and that these translocated bacteria are non-pathogenic, even in immunocompromised animals. They have shown that ingestion of these food-grade bacteria carrying a gene of interest results in high-level expression specifically in tumours. Potential for strain optimisation exists through re-isolating vector with increased efficiencies from experimental tumours, as has been accomplished with other tumour targeting bacteria [26, 30, 27]. Overall, this strategy represents a novel, safe and non-invasive vector system, with the potential to deliver therapeutic or diagnostic agents systemically. The vector could be cleared by antibiotic administration. The current invention could also be used in non-cancer related physiological studies as a reporting system for investigations on translocation and related effects, especially since translocation to organs occurred at the same level in the absence or presence of tumour. The route of administration of a therapeutic is important in clinical and commercial settings. Direct intratumoural administration of bacterial vectors restricts usage to accessible tumours, and while intravenous administration facilitates targeting of systemic tumour sites, the oral route is amenable to administering much higher doses of bacteria safely and is likely to be more appealing when applied to the clinical setting due to ease of drug application. Furthermore, pharmaceutical industry dogma displays a preference for the oral route of administration.

The words "comprises/comprising" and the words "having/including" when used herein with reference to the present invention are used to specify the presence of stated features, integers, steps or components but does not preclude the presence or addition of one or more other features, integers, steps, components or groups thereof It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

REFERENCES

1. Fujimori M, Amano J, Taniguchi S. The genus *Bifidobacterium* for cancer gene therapy. *Curr Opin Drug Discov Devel* 2002; 5(2): 200-203.
2. Li Z, Fallon J, Mandeli J, Wetmur J, Woo S L. A genetically enhanced anaerobic bacterium for oncopathic therapy of pancreatic cancer. *J Natl Cancer Inst* 2008; 100(19): 1389-1400.
3. Vassaux G, Nitcheu J, Jezzard S, Lemoine N R. Bacterial gene therapy strategies. *J Pathol* 2006; 208(2): 290-298.
4. Wei M Q, Mengesha A, Good D, Anne J. Bacterial targeted tumour therapy-dawn of a new era. *Cancer Lett* 2008; 259(1): 16-27.

5. Yu Y A, Shabahang S, Timiryasova T M, Zhang Q, Beltz R, Gentschev I et al. Visualization of tumors and metastases in live animals with bacteria and vaccinia virus encoding light-emitting proteins. *Nat Biotechnol* 2004; 22(3): 313-320.
6. Zhao M, Yang M, Li X M, Jiang P, Baranov E, Li S et al. Tumor-targeting bacterial therapy with amino acid auxotrophs of GFP-expressing *Salmonella typhimurium*. *Proc Nad Acad Sci* USA 2005; 102(3): 755-760.
7. Morrissey D, O'Sullivan, G C, Tangney, M. Tumour targeting with systemically administered bacteria. *Curr Gene Ther* 2010; 10(1).
8. Tangney M, Gahan, C G M. *Listeria monocytogenes* as a vector for anti-cancer therapies. *Curr Gene Ther* 2010; 10(1).
9. van Pijkeren J, Morrissey D, Cronin M, Rajendran S, O'Sullivan G, Gahan C et al. A novel *Listeria monocytogenes*-based DNA delivery system for cancer gene therapy. *Human Gene Therapy* 2010; 21(3).
10. Leahy S C, Higgins D G, Fitzgerald G F, van Sinderen D. Getting better with bifidobacteria. *J Appl Microbiol* 2005; 98(6): 1303-1315.
11. Li X, Fu G F, Fan Y R, Liu W H, Liu X J, Wang J J et al. *Bifidobacterium* adolescentis as a delivery system of endostatin for cancer gene therapy: selective inhibitor of angiogenesis and hypoxic tumor growth. *Cancer Gene Ther* 2003; 10(2): 105-111.
12. Nakamura T, Sasaki T, Fujimori M, Yazawa K, Kano Y, Amano J et al. Cloned cytosine deaminase gene expression of *Bifidobacterium longum* and application to enzyme/prodrug therapy of hypoxic solid tumors. *Biosci Biotechnol Biochem* 2002; 66(11): 2362-2366.
13. Yi C, Huang Y, Guo Z Y, Wang S R. Antitumor effect of cytosine deaminase/5-fluorocytosine suicide gene therapy system mediated by *Bifidobacterium infantis* on melanoma. *Acta Pharmacol Sin* 2005; 26(5): 629-634.
14. Balzan S, de Almeida Quadros C, de Cleva R, Zilberstein B, Cecconello I. Bacterial translocation: overview of mechanisms and clinical impact. *J Gastroenterol Hepatol* 2007; 22(4): 464-471.
15. Berg R D. Bacterial translocation from the gastrointestinal tract. *Adv Exp Med Biol* 1999; 473: 11-30.
16. Ishibashi N, Yamazaki S. Probiotics and safety. *Am J Clin Nutr* 2001; 73(2 Suppl): 465S-470S.
17. Riedel C U, Monk I R, Casey P G, Morrissey D, O'Sullivan G C, Tangney M et al. Improved luciferase tagging system for *Listeria monocytogenes* allows real-time monitoring in vivo and in vitro. *Appl Environ Microbiol* 2007; 73(9): 3091-3094.
18. Cronin M, Sleator R D, Hill C, Fitzgerald G F, van Sinderen D. Development of a luciferase-based reporter system to monitor *Bifidobacterium breve* UCC2003 persistence in mice. *BMC Microbiol* 2008; 8: 161.
19. Luyer M D, Buurman W A, Hadfoune M, Wolfs T, van't Veer C, Jacobs J A et al. Exposure to bacterial DNA before hemorrhagic shock strongly aggravates systemic inflammation and gut barrier loss via an IFN-gamma-dependent route. *Ann Surg* 2007; 245(5): 795-802.
20. McKay D M, Watson J L, Wang A, Caldwell J, Prescott D, Ceponis P M et al. Phosphatidylinositol 3'-kinase is a critical mediator of interferon-gamma-induced increases in enteric epithelial permeability. *J Pharmacol Exp Ther* 2007; 320(3): 1013-1022.
21. Haller D, Blum S, Bode C, Hammes W P, Schiffrin E J. Activation of human peripheral blood mononuclear cells by nonpathogenic bacteria in vitro: evidence of NK cells as primary targets. *Infect Immun* 2000; 68(2): 752-759.
22. Haller D, Bode C, Hammes W P, Pfeifer A M, Schiffrin E J, Blum S. Non-pathogenic bacteria elicit a differential cytokine response by intestinal epithelial cell/leucocyte co-cultures. *Gut* 2000; 47(1): 79-87.
23. Iyer M, Sato M, Johnson M, Gambhir S S, Wu L. Applications of molecular imaging in cancer gene therapy. *Curr Gene Ther* 2005; 5(6): 607-618.
24. Lemmon M J, van Zijl P, Fox M E, Mauchline M L, Giaccia A J, Minton N P et al. Anaerobic bacteria as a gene delivery system that is controlled by the tumor microenvironment. *Gene Ther* 1997; 4(8): 791-796.
25. Yazawa K, Fujimori M, Amano J, Kano Y, Taniguchi S. *Bifidobacterium longum* as a delivery system for cancer gene therapy: selective localization and growth in hypoxic tumors. *Cancer Gene Ther* 2000; 7(2): 269-274.
26. Nagakura C, Hayashi K, Zhao M, Yamauchi K, Yamamoto N, Tsuchiya H et al. Efficacy of a genetically-modified *Salmonella typhimurium* in an orthotopic human pancreatic cancer in nude mice. *Anticancer Res* 2009; 29(6): 1873-1878.
27. Zhao M, Yang M, Ma H, Li X, Tan X, Li S et al. Targeted therapy with a *Salmonella typhimurium* leucine-arginine auxotroph cures orthotopic human breast tumors in nude mice. *Cancer Res* 2006; 66(15): 7647-7652.
28. Hayashi K, Zhao M, Yamauchi K, Yamamoto N, Tsuchiya H, Tomita K et al. Cancer metastasis directly eradicated by targeted therapy with a modified *Salmonella typhimurium*. *J Cell Biochem* 2009; 106(6): 992-998.
29. Hayashi K, Zhao M, Yamauchi K, Yamamoto N, Tsuchiya H, Tomita K et al. Systemic targeting of primary bone tumor and lung metastasis of high-grade osteosarcoma in nude mice with a tumor-selective strain of *Salmonella typhimurium*. *Cell Cycle* 2009; 8(6): 870-875.
30. Zhao M, Geller J, Ma H, Yang M, Penman S, Hoffman R M. Monotherapy with a tumor-targeting mutant of *Salmonella typhimurium* cures orthotopic metastatic mouse models of human prostate cancer. *Proc Natl Acad Sci USA* 2007; 104(24): 10170-10174.
31. Fujimori M. Genetically engineered bifidobacterium as a drug delivery system for Systemic therapy of metastatic breast cancer patients. *Breast Cancer* 2006; 13(1): 27-31.
32. Menard O, Butel M J, Gaboriau-Routhiau V, Waligora-Dupriet A J. Gnotobiotic mouse immune response induced by *Bifidobacterium* sp. strains isolated from infants. *Appl Environ Microbiol* 2008; 74(3): 660-666.
33. Fu G F, Li X, Hou Y Y, Fan Y R, Liu W H, Xu G X. *Bifidobacterium longum* as an oral delivery system of endostatin for gene therapy on solid liver cancer. *Cancer Gene Ther* 2005; 12(2): 133-140.
34. Penn R L, Maca R D, Berg R D. Increased translocation of bacteria from the gastrointestinal tracts of tumor-bearing mice. *Infect Immun* 1985; 47(3): 793-798.
35. Penn R L, Nguyen V Q, Specian R D, Stevens P, Berg R D. Interleukin-2 enhances the translocation of *Escherichia coli* from the intestines to other organs. *J Infect Dis* 1991; 164(6): 1168-1172.
36. Berg R D. Translocation of enteric bacteria in health and disease. *Curr Stud Hematol Blood Transfus* 1992; (59): 44-65.
37. Owens W E, Berg R D. Bacterial translocation from the gastrointestinal tract of athymic (nu/nu) mice. *Infect Immun* 1980; 27(2): 461-467.
38. Berg R D, Garlington A W. Translocation of certain indigenous bacteria from the gastrointestinal tract to the mesenteric lymph nodes and other organs in a gnotobiotic mouse model. *Infect Immun* 1979; 23(2): 403-411.

39. Berg R D, Owens W E Inhibition of translocation of viable *Escherichia coli* from the gastrointestinal tract of mice by bacterial antagonism. *Infect Immun* 1979; 25(3): 820-827.
40. Steffen E K, Berg R D. Relationship between cecal population levels of indigenous bacteria and translocation to the mesenteric lymph nodes. *Infect Immun* 1983; 39(3): 1252-1259.
41. Steffen E K, Berg R D, Deitch E A. Comparison of translocation rates of various indigenous bacteria from the gastrointestinal tract to the mesenteric lymph node. *J Infect Dis* 1988; 157(5): 1032-1038.
42. Liong M T. Safety of probiotics: translocation and infection. *Nutr Rev* 2008; 66(4): 192-202.
43. Rodriguez A V, Baigori M D, Alvarez S, Castro G R, Oliver G. Phosphatidylinositol-specific phospholipase C activity in *Lactobacillus rhamnosus* with capacity to translocate. *FEMS Microbiol Lett* 2001; 204(1): 33-38.
44. van der Waaij D, Berghuis-de Vries J M, Lekkerkerk-van der W. Colonization resistance of the digestive tract and the spread of bacteria to the lymphatic organs in mice. *J Hyg (Lond)* 1972; 70(2): 335-342.
45. Wells C L. Relationship between intestinal microecology and the translocation of intestinal bacteria. *Antonie Van Leeuwenhoek* 1990; 58(2): 87-93.
46. Berg R D. Bacterial translocation from the intestines. *Jikken Dobutsu* 1985; 34(1): 1-16.
47. Yamazaki S, Machii K, Tsuyuki S, Momose H, Kawashima T, Ueda K Immunological responses to monoassociated *Bifidobacterium longum* and their relation to prevention of bacterial invasion. *Immunology* 1985; 56(1): 43-50.
48. Sedman P C, Macfie J, Sagar P, Mitchell C J, May J, Mancey-Jones B et al. The prevalence of gut translocation in humans *Gastroenterology* 1994; 107(3): 643-649.
49. Pavan S, Desreumaux P, Mercenier A. Use of mouse models to evaluate the persistence, safety, and immune modulation capacities of lactic acid bacteria. *Clin Diagn Lab Immunol* 2003; 10(4): 696-701.
50. Tancrede C H, Andremont A O. Bacterial translocation and gram-negative bacteremia in patients with hematological malignancies. *J Infect Dis* 1985; 152(1): 99-103.
51. Zhou J S, Shu Q, Rutherfurd K J, Prasad J, Gopal P K, Gill H S. Acute oral toxicity and bacterial translocation studies on potentially probiotic strains of lactic acid bacteria.
52. Riedel C U M I, Casey P G, Morrissey D, O'Sullivan G C, Tangney M, Hill C, Gahan C G. Improved luciferase tagging system for *Listeria monocytogenes* allows real-time monitoring in vivo and in vitro. *Appl Environ Microbiol* 2007; 2007;73:3091-3094. doi: 10.1128/AEM.02940-06. [PubMed].
53. Simpson P J, Stanton C, Fitzgerald G F, Ross R P. Genomic diversity and relatedness of bifidobacteria isolated from a porcine cecum. *J Bacteriol* 2003; 185(8): 2571-2581.
54. Turroni F, Foroni E, Pizzetti P, Giubellini V, Ribbera A, Merusi P et al. Exploring the diversity of the bifidobacterial population in the human intestinal tract. *Appl Environ Microbiol* 2009; 75(6): 1534-1545.
55. O'Connell Motherway M, Fitzgerald G F, Neirynck S, Ryan S, Steidler L, van Sinderen D. Characterization of ApuB, an extracellular type II amylopullulanase from *Bifidobacterium breve* UCC2003. *Appl Environ Microbiol* 2008; 74(20): 6271-6279.
56. Yashui H, Mike A, Ohwaki M. Immunogenicity of *Bifidobacterium breve* and change in Antibody production in Peyer's pathces after oral administration. *J Dairy Sci* 1989; 72(1): 30-35.
57. Moriyama E H, Niedre M J, Jarvi M T, Mocanu J D, Moriyama Y, Subarsky P et al. The influence of hypoxia on bioluminescence in luciferase-transfected gliosarcoma tumor cells in vitro. *Photochem Photobiol Sci* 2008; 7(6): 675-680.
58. Wiles S, Pickard K M, Peng K, MacDonald T T, Frankel G. In vivo bioluminescence imaging of the murine pathogen Citrobacter rodentium. *Infect Immun* 2006; 74(9): 5391-5396.

The invention claimed is:

1. A method of delivering an agent to extraintestinal sites in the body of a mammalian subject comprising orally administering a composition to the subject, wherein the composition comprises effective colony forming units of viable *Bifi-* dobacterium breve* UCC2003 comprising a vector which expresses an exogenous gene that encodes the agent, wherein the *Bifidobacterium breve* UCC2003 in the composition translocates from the gastrointestinal tract to the extraintestinal sites in the body of the subject and locally replicates and expresses the exogenous gene, thereby delivering the agent to the extraintestinal sites.

2. The method of claim 1, wherein the extraintestinal sites are tumour sites.

3. The method of claim 1, wherein the agent is a tumour suppressing agent.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
ggtgtgaaag tccatcgct                                                  19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gtctgccaag gcatccacca                                                 20
```